United States Patent
Nikolskiy et al.

(10) Patent No.: US 11,585,766 B2
(45) Date of Patent: Feb. 21, 2023

(54) CT SCANNER CALIBRATION

(71) Applicant: James R. Glidewell Dental Ceramics, Inc., Newport Beach, CA (US)

(72) Inventors: Sergey Nikolskiy, Coto de Caza, CA (US); Fedor Chelnokov, Khimki (RU); Grant Karapetyan, Moscow (RU)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

(21) Appl. No.: 16/887,437

(22) Filed: May 29, 2020

(65) Prior Publication Data

US 2021/0372950 A1 Dec. 2, 2021

(51) Int. Cl.
*G01D 18/00* (2006.01)
*G01N 23/046* (2018.01)
(Continued)

(52) U.S. Cl.
CPC ............. *G01N 23/046* (2013.01); *A61B 6/14* (2013.01); *G01N 23/083* (2013.01);
(Continued)

(58) Field of Classification Search
CPC .............. H05K 999/99; G01N 23/046; G01N 2223/419; G01N 2223/303; G01N 2223/3035; G01N 23/083; G01N 2223/04; G01N 23/04; G01N 23/10; G01N 23/087; G01N 2223/501; G01N 33/02; G01N 33/24; G01N 2223/3303; G01N 2223/616; G01B 15/00; G01B 21/045; G01B 21/042; G01B 3/30; G01B 15/02; A61B 17/15; A61B 17/155; A61B 17/157; A61B 17/1666; A61B 17/17; A61B 17/1703; A61B 17/1742; A61B 17/1764; A61B 17/1775; A61B 17/1778; A61B 2017/00216; A61B 2017/568; A61B 2034/104; A61B 2034/107; A61B 2034/2048; A61B 2034/2055; A61B 2034/2059; A61B 6/032; A61B 6/583; A61B 6/584; A61B 6/08; A61B 6/547; A61B 6/14; A61B 6/03; A61B 6/465; A61B 6/5247; A61B 17/154; A61B 17/1714; A61B 17/1746; A61B 17/1757; A61B 2017/00203; A61B 2017/00207; A61B 2017/00221; A61B 3/102;
(Continued)

(56) References Cited

U.S. PATENT DOCUMENTS 5,872,829 A * 2/1999 Wischmann ........... A61B 6/583
378/20
6,813,374 B1 11/2004 Karimi et al.
(Continued)

OTHER PUBLICATIONS

Kai Yang et al., A geometric calibration method for cone beam CT systems, National Institutes of Health, NIH Public Access, Author Manuscript, Med Phys., Jun. 2006; 33(6); 1695-1706, 40 pages.
(Continued)

*Primary Examiner* — Irakli Kiknadze
(74) *Attorney, Agent, or Firm* — Charles Fowler

(57) ABSTRACT

A system and method can determine one or more CT scanner calibration parameters from a plurality of calibration object projections in a plurality of radiographs.

20 Claims, 18 Drawing Sheets

(51) Int. Cl.
*G01N 23/083* (2018.01)
*A61B 6/14* (2006.01)
*A61B 6/00* (2006.01)

(52) U.S. Cl.
CPC ... *G01N 2223/04* (2013.01); *G01N 2223/303* (2013.01); *G01N 2223/419* (2013.01)

(58) Field of Classification Search
CPC ....... A61B 6/037; A61B 6/4258; A61B 5/055; A61B 5/7267; A61B 5/0066; A61B 5/0075; A61B 5/742; A61B 5/7475; A61B 6/481; A61B 6/504; A61B 6/5205; A61B 8/12; A61B 8/14; A61B 5/0035; A61B 5/0059; A61B 5/7257; A61B 5/7264; A61B 6/5282; A61B 6/4085; A61B 6/06; A61B 6/4291; A61B 6/563; A61B 6/4035; A61B 6/4014; A61B 6/0492; A61B 6/5211; A61B 6/5294; A61B 6/484; A61B 6/463; A61B 6/582; A61B 6/0407; G01T 7/005; G01T 1/1642; G01T 1/172; G01T 1/2985; G01T 1/246; G01T 1/247; G01T 1/1647; G01T 1/1603; G01T 1/1663; G01T 1/2992; G01T 1/20182; G01T 1/243; G02B 2027/0138; G02B 2027/0141; G02B 27/0172; G06T 2200/24; G06T 2207/10116; G06T 2207/30036; G06T 2207/30204; G06T 3/40; G06T 7/33; G06T 15/08; G06T 15/20; G06T 7/0012; G06T 7/246; G06T 11/008; G06T 2207/30012; G06T 2211/40; G06T 11/005; G06T 11/006; G06T 7/70; B25J 9/1697; G16H 50/30; G16H 50/20; G16H 30/40; G16H 30/20; H01J 35/045; H01J 2235/068; H01J 35/04; G06K 2009/363; G06K 2209/05; G06K 9/3216; G06K 9/36; G06K 9/6215; G06K 9/627; G06K 9/6298; G06K 9/4638; G06K 9/4633; G06K 9/2054; G06K 9/6202; G06K 9/6259; G06K 9/6267; G06K 2009/6213; G06K 9/3241; G06K 9/38; G06K 9/4652; G06K 9/4661; G01V 5/005; G01V 5/0041
USPC ......................................... 378/4, 19, 62, 207
See application file for complete search history.

(56) References Cited

U.S. PATENT DOCUMENTS

| | | | |
|---|---|---|---|
| 6,991,371 B2* | 1/2006 | Georgeson | G01T 1/169 378/207 |
| 7,700,909 B2 | 4/2010 | Holt | |
| 7,922,390 B2 | 4/2011 | Holt et al. | |
| 8,777,485 B2 | 7/2014 | Holt | |
| 10,539,515 B2* | 1/2020 | Fischer | G01T 7/005 |
| 10,974,074 B2* | 4/2021 | Hale | A61N 5/1075 |
| 11,222,435 B2 | 1/2022 | Nikolskiy et al. | |
| 2005/0094771 A1* | 5/2005 | Basu | A61B 6/032 378/207 |
| 2005/0113680 A1 | 5/2005 | Ikeda et al. | |
| 2006/0110068 A1 | 5/2006 | Lou et al. | |
| 2006/0291612 A1 | 12/2006 | Nishide et al. | |
| 2007/0274456 A1 | 11/2007 | Holt | |
| 2010/0195893 A1 | 8/2010 | Fuchigami et al. | |
| 2013/0016125 A1 | 1/2013 | Mainguet | |
| 2013/0223587 A1 | 8/2013 | Moriyasu | |
| 2013/0243276 A1 | 9/2013 | Souza et al. | |
| 2014/0169650 A1 | 6/2014 | Sakimoto et al. | |
| 2015/0221080 A1 | 8/2015 | Yamamoto | |
| 2015/0305696 A1 | 10/2015 | Yamakawa et al. | |
| 2017/0112462 A1* | 4/2017 | O'Hare | G01T 7/005 |
| 2017/0154413 A1 | 6/2017 | Yu et al. | |
| 2017/0294034 A1 | 10/2017 | Zhou et al. | |
| 2017/0301114 A1* | 10/2017 | Yang | A61B 6/502 |
| 2017/0311918 A1 | 11/2017 | Qi et al. | |
| 2017/0345190 A1 | 11/2017 | Shi et al. | |
| 2018/0132982 A1 | 5/2018 | Nikolskiy et al. | |
| 2019/0235100 A1 | 8/2019 | Kimmig | |
| 2021/0072168 A1* | 3/2021 | Sasaki | G06T 7/60 |
| 2021/0085279 A1* | 3/2021 | Asano | G01N 23/046 |
| 2022/0160323 A1 | 5/2022 | Maur et al. | |

OTHER PUBLICATIONS

Richard Radke et al., Efficently Estimating Projective Transformations, dated Jun. 27, 2001, in 32 pages.

David Walter et al., Photon Counting and Energy Discriminating X-Ray Detectors—Benefits and Applications, 19th World Conference on Non-Destructive Testing 2016, in 10 pages.

A.C. Kak et al., Principles of Computerized Tomographic Imaging, Principles of Computerized Tomographic Imaging, IEEE Press, 1988. (Entire Book).

Yongsheng Pan et al., Automatic Detection of Rotational Centers Using GPU from Projection Data for micro-tomography in Synchrotron Radiation, Medical Imaging 2012: Physics of Medical Imaging, Proc. of SPIE vol. 8313, 331328 © 2012 SPIE—CCC code: 1605-7422/12/$18 doi: 10.1117/12.911561, proceedings. spiedigitallibrary.org on Nov. 23, 2016, in 9 pages.

Ghia T. Vo et al., Reliable method for calculating the center of rotation in parallel-beam tomography, Diamond Light Source, Harwell Science and Innovation Campus, Didcot, Oxfordshire, OX11 0DE, UK, published Jul. 30, 2014, vol. 22, No. 16, DOI: 10.1364/OE. 22.019078, Optic Express 19078, in 9 pages.

* cited by examiner

CT SCANNER CALIBRATION

BACKGROUND

A computed tomography scan ("CT scan") typically involves placing a physical object on a rotating platform inside a Computed Tomography scanner (CT scanner) between an x-ray source and x-ray detector and rotating the object around an axis of rotation to generate radiographs from the x-rays detected by the detector. Conventionally, the CT scanner can tomographically reconstruct the radiographs into a 3D representation of the object scanned ("CT reconstruction"). One example of CT reconstruction can be found in, for example, in the publication *Principles of Computerized Tomographic Imaging* (A. C. Kak and Malcolm Slaney, *Principles of Computerized Tomographic Imaging*, IEEE Press, 1988), the entirety of which is incorporated by reference herein. Other types of CT reconstruction can also be performed.

CT scanners are typically configured with calibration parameters which are provided to reconstruction algorithms to generate the reconstructed image. However, over time, CT scanners can be subject to factors that can alter physical component alignment and relationships between them. These factors can render the initial parameters ineffective to reconstruct an accurate or clear image. Accordingly, CT scanners can need calibration. Although attempts at determining calibration parameters have been made, they can be imprecise and inaccurate and inflexible in terms of placement of calibration artifacts.

SUMMARY

Disclosed is a method of determining CT calibration settings, the method including receiving a plurality of radiographs from a CT scanner, each of the plurality of radiographs comprising a plurality of calibration object projections; and determining one or more CT scanner calibration parameters from a plurality of calibration object projections in the plurality of radiographs.

Also disclosed is a system for determining CT calibration settings, including: a processor, a computer-readable storage medium comprising instructions executable by the processor to perform steps including: receiving a plurality of radiographs from a CT scanner, each of the plurality of radiographs comprising a plurality of calibration object projections; and determining one or more CT scanner calibration parameters from a plurality of calibration object projections in the plurality of radiographs.

Also disclosed is a non-transitory computer readable medium storing executable computer program instructions to determine CT calibration settings, the computer program instructions comprising instructions for: receiving a plurality of radiographs from a CT scanner, each of the plurality of radiographs including a plurality of calibration objects arranged with at least one artifact object; and determining one or more CT scanner calibration parameters from a plurality of calibration object projections in the plurality of radiographs.

BRIEF DESCRIPTION OF THE DRAWINGS

FIG. 4(*b*) shows a schematic diagram illustrating a side view of the CT scanning system.

FIG. 4(*c*) shows an illustration of a plane view of a detector.

FIG. 10(*b*) is an illustration of the detector plane.

DETAILED DESCRIPTION

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the following description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

Figure 1:
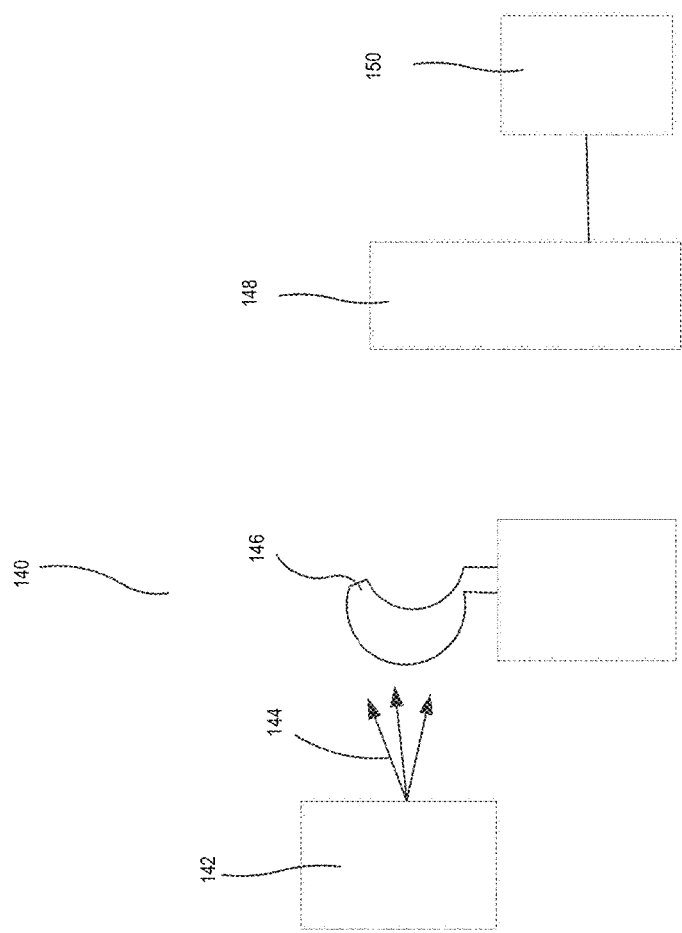
FIG. 1 shows a schematic diagram of a computed tomography (CT) scanning system.

A computed tomography (CT) scanner uses x-rays to make a detailed image of an object. A plurality of such images are then combined to form a 3D model of the object. A schematic diagram of an example of a CT scanning system 140 is shown in FIG. 1. The CT scanning system 140 includes a source of x-ray radiation 142 that emits an x-ray beam 144. An object 146 being scanned is placed between the source 142 and an x-ray detector 148. In some embodiments, the object can be any object that can, for example, fit in a CT scanning system and be penetrated by x-rays. The x-ray detector 148, in turn, is connected to a processor 150 that is configured to receive the information from the detector 148 and to convert the information into a digital image file. Those skilled in the art will recognize that the processor 150 may comprise one or more computers that may be directly connected to the detector, wirelessly connected, connected via a network, or otherwise in direct or indirect communication with the detector 148.

An example of a suitable scanning system 140 includes a Nikon Model XTH 255 CT Scanner (Metrology) which is commercially available from Nikon Corporation. The example scanning system includes a 225 kV microfocus x-ray source with a 3 μm focal spot size to provide high performance image acquisition and volume processing. The processor 150 may include a storage medium that is configured with instructions to manage the data collected by the scanning system. A particular scanning system is described for illustrative purposes; any type/brand of CT scanning system can be utilized.

Figure 2:
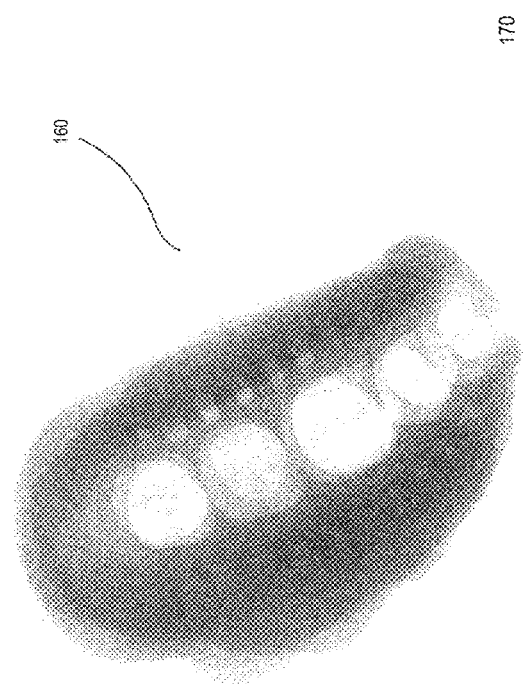
FIG. 2 shows a 2-dimensional (2D) radiographic image of a dental impression tray containing a dental impression.

One example of CT scanning is described in U.S. Patent Application No. US20180132982A1 to Nikolskiy et al., which is hereby incorporated in its entirety by reference. As noted above, during operation of the scanning system 140, the object 146 is located between the x-ray source 142 and the x-ray detector 148. A series of images of the object 146 are collected by the processor 150 as the object 146 is rotated in place between the source 142 and the detector 146. An example of a single radiograph 160 is shown in FIG. 2. The radiograph 160 and all radiographs described herein are understood to be digital. In one embodiment, a series of 720 images can be collected as the object 146 is rotated in place between the source 142 and the detector 148. In other embodiments, more images or fewer images may be collected as will be understood by those skilled in the art. In some embodiments, radiographs can be referred to as projection images.

Figure 3:
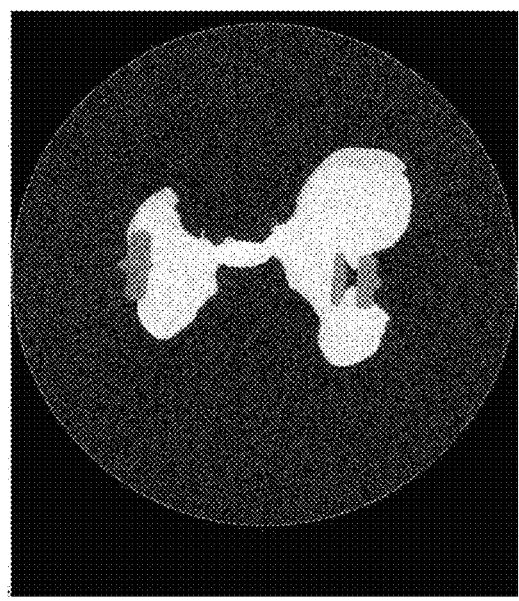
FIG. 3 shows a cross-section of a 3-dimensional (3D) volumetric image.

The plurality of radiographs 160 of the object 146 are generated by and stored within a storage medium contained within the processor 150 of the scanning system 140, where they may be used by software contained within the processor to perform additional operations. For example, in an embodiment, the plurality of radiographs 160 can undergo tomographic reconstruction in order to generate a 3D virtual image 170 (see FIG. 3) from the plurality of 2D radiographs 160 generated by the scanning system 140. In the embodiment shown in FIG. 3, the 3D virtual image 170 is in the form of a volumetric image or volumetric density file (shown in cross-section in FIG. 3) that is generated from the plurality of radiographs 160 by way of a CT reconstruction algorithm associated with the scanning system 140. One type of CT reconstruction algorithm can be the filtered backprojection algorithm as described in the *Principles of Computerized Tomographic Imaging* publication. Other types of CT reconstruction algorithms known in the art can also be used.

Figure 4A:
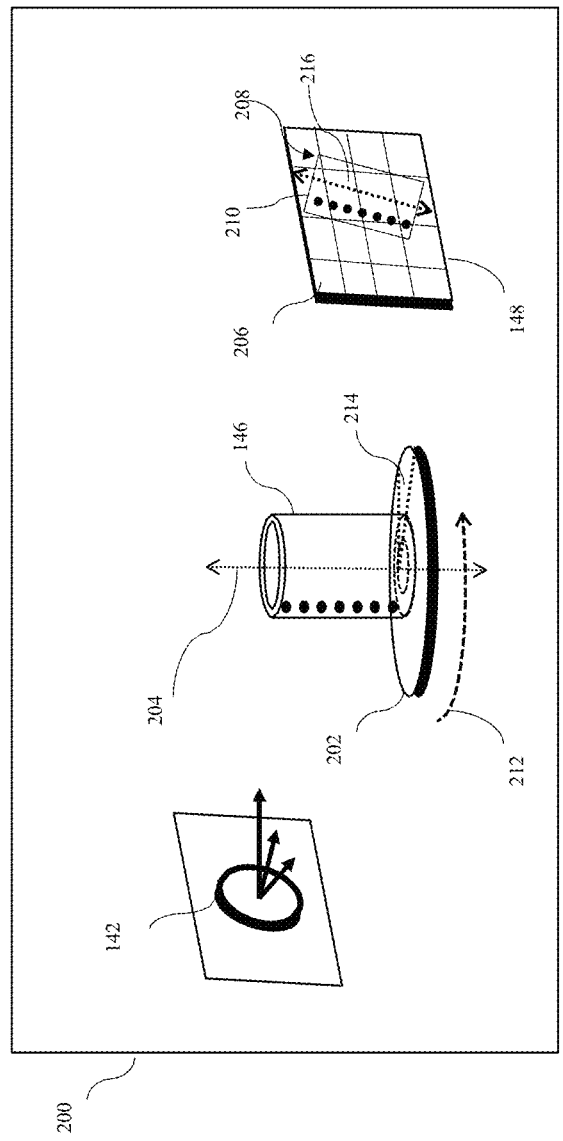
FIG. 4(*a*) shows a 3D schematic diagram illustrating a CT scanning system.

FIG. 4(a) is an illustration of portions of a CT scanning system as discussed previously. Certain features of the CT scanning system are not shown for clarity. Other conventional CT scanning systems known in the art can also be utilized. Conventionally, the physical object 146 to be scanned is placed inside the CT scanner 200 on top of a rotational platform 202 between an x-ray source 142 and x-ray detector 148. The physical object 146 is exposed to x-rays generated by the x-ray source 142 that travel from the x-ray source 142 through the physical object 146 and to the x-ray detector 148. In some embodiments, the x-rays generated by the x-ray source 142 can generate a cone-beam shape of x-rays. The x-ray detector 148 conventionally includes a detector pixel array 206 (row of detector pixels and column of detector pixels) which detects any incident x-rays to generate a radiograph 208, for example. In some embodiments, the x-ray detector 148 can include an array resolution of 1,000×1,000 pixels, for example. In some embodiments, the number of pixels can be at least 1 million pixels, for example. Other numbers of pixels can also be present. Other array resolutions are also possible. Conventionally, as the physical object 146 is rotated around an axis of rotation 204, the x-ray detector 148 detects x-rays incident on each pixel such as detector pixel 210 (and any other detector pixels) at each rotational position to generate multiple radiographs. The x-ray detector 148 can detect a photon count at each pixel for each radiograph generated at each rotational position. In some embodiments, the possible photon count can be any value. In some embodiments, the possible photon count range can be anywhere from 0 to 65535 photons per pixel, for example. Other photon count ranges per pixel are also possible. In some embodiments, the physical object 146 can be rotated 360 degrees once, and the direction of rotation 212 can be either clockwise or counterclockwise. Conventional/standard CT scanning systems allow setting the total number of radiographs desired prior to scanning. Conventionally, the x-ray detector 148 detects and stores a radiograph 208 every rotational degree 214 based on the total number of radiographs desired. For example, the rotational degree 214 can conventionally be determined as follows by the standard CT scanner 200: 360 degrees divided by the total number of radiographs desired, for example. In some embodiments, the total number of radiographs can be at least 600 radiographs, for example. However, any number of radiographs can be generated. The x-ray detector 148 conventionally detects and stores the radiograph 208 as well as the photon count for every detector pixel such as detector pixel 210. An example of conventional photon counting and x-ray detectors can be found, for example, in *Photon Counting and Energy Discriminating X-Ray Detectors—Benefits and Applications* (David WAL- TER, Uwe ZSCHERPEL, Uwe EWERT, BAM Bundesanstalt für Materialforschung und-prüfung, Berlin, Germany, 19th World Conference on Non-Destructive Testing, 2016), the entirety of which is incorporated by reference herein. A single CT scan can therefore generate multiple radiographs in some embodiments in a single CT scan.

Figure 4B:
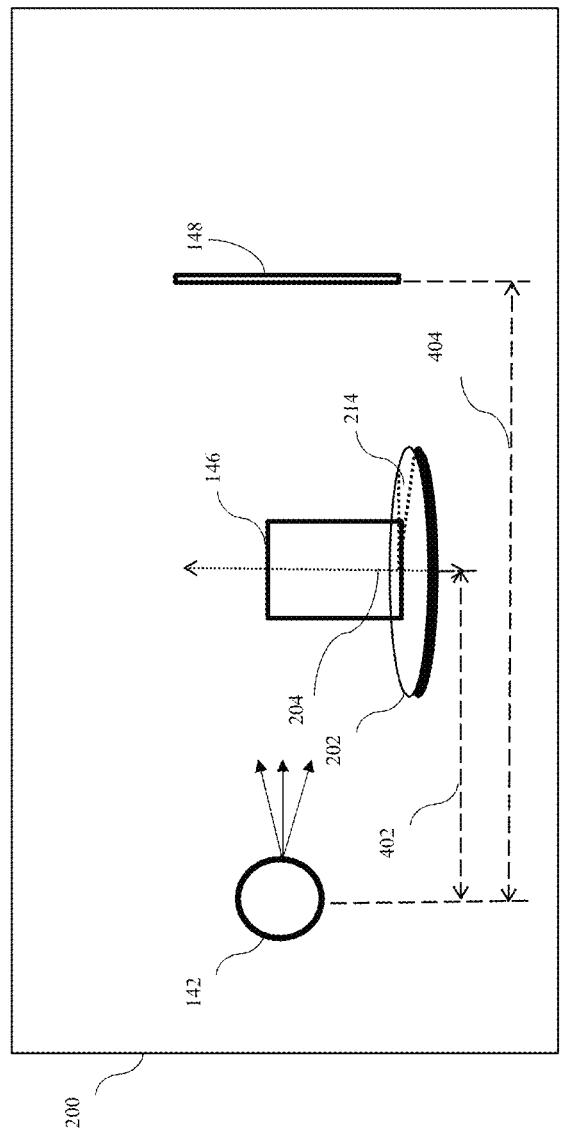
Figure 4E:
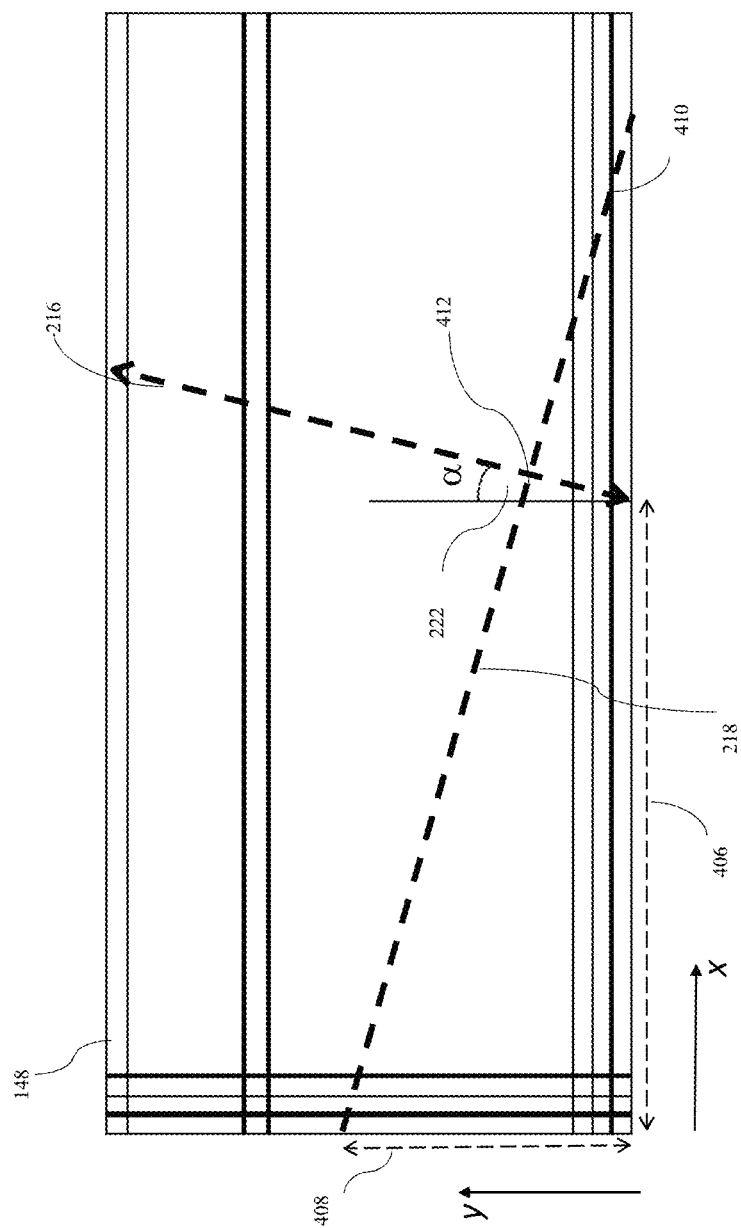

Some embodiments include a method of determining CT calibration settings. CT calibration settings can include, for example, an axis of rotation distance d 402, which can be the distance from the x-ray source 142 to the axis of rotation 204 as illustrated in FIG. 4(b). Another CT calibration setting can include, for example, a detector distance D 404, which can be, for example, the distance from the x-ray source 142 to the x-ray detector 148, as also illustrated in FIG. 4(b). CT calibration settings can also include, for example, a projected rotation axis 216, inclination angle 222, projected rotation axis horizontal shift $u_0$ 406, and a vertical shift $v_0$ 408 as illustrated in FIG. 4(c). The vertical shift $v_0$ 408 can be based, for example, on a line 410 perpendicular to the projected rotation axis passing through a closest point 412 to x-ray source 142 on the projected rotation axis 216.

In some embodiments, the physical object 146 can be one or more calibration objects arranged in a calibration object holder, for example. In some embodiments, the calibration object holder can be any rigid fixture that can hold calibration objects vertically (i.e. along the rotation axis) in a fixed position, spaced apart from one another, and such that the calibration objects encounter x-rays generated from the x-ray source 142 as the calibration object holder is rotated along with the rotational platform 202 on top of which it is placed.

Figure 5:
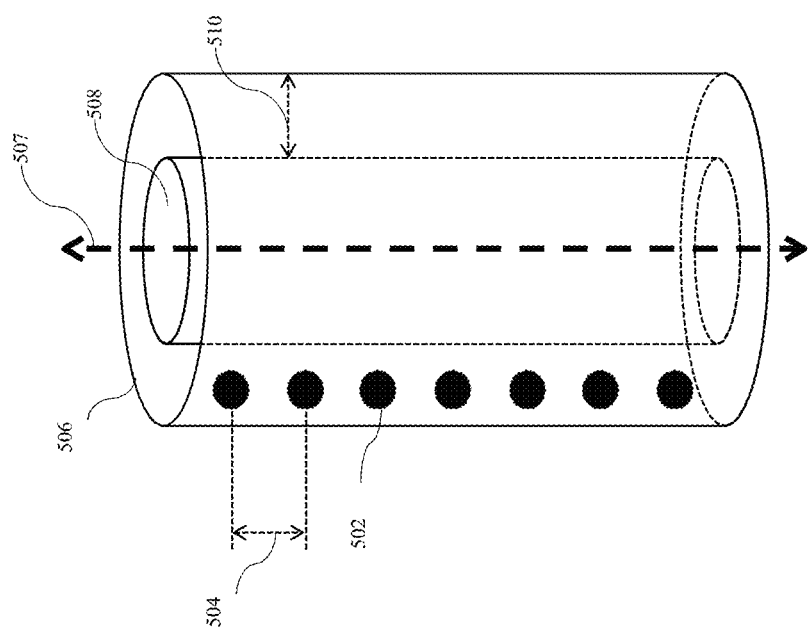
FIG. 5 shows a 3D schematic diagram illustrating calibration object projections and a calibration object holder projection.

FIG. 5 illustrates one example of several calibration objects including first calibration object 502 arranged in a calibration object holder 504. Although seven calibration objects are illustrated in the figure, this is only an example; more or fewer calibration objects can be used. The calibration objects can be made of any type of radio-opaque material in some embodiments. For example, the calibration objects can be made of steel. Any other type of radio-opaque material can be used. The calibration objects can be any size. In some embodiments, smaller calibration object sizes can be preferable. In some embodiments, the calibration objects can have a radius of 2 mm in the case of spherical calibration objects, for example. In some embodiments, the calibration objects can be spherical in shape, for example. However, other shapes can also be used for the calibration objects. In some embodiments, the calibration objects can be spaced apart by any calibration object spacing distance 504, for example. The calibration object spacing distance 504 between the calibration objects can be the same distance in some embodiments, for example. The calibration object spacing distance between the calibration objects can vary in distance in some embodiments, for example.

In some embodiments, the calibration objects can be arranged in a calibration object holder 506, for example. The calibration object holder 506 can be, for example, cylindrical in shape in some embodiments, for example, with a hollow center 508. In some embodiments, the walls 510 of the calibration object holder 506 are preferably thin to improve its transparency and improve determination of a center of each calibration object, for example, but thick enough to house the calibration objects, for example. In some embodiments, the calibration object holder 506 can be dimensioned such that the calibration objects are as far away from the axis of rotation, for example by making the calibration object holder 506 wide. In some embodiments, the calibration object holder 506 can be, for example, 50 mm outer radius and 200 mm in height. However, the calibration object holder 506 can be any other shape and can be any other dimensions. The calibration object holder 506 can be made of a radio-translucent material in some embodiments. For example, the calibration object holder 506 can be made of glass, or other suitable radio-translucent material. For example, the calibration object holder 506 can be made of polycarbonate, or other suitable radio-translucent material, and the calibration objects can be pressed into the polycarbonate. In some embodiments, the calibration object holder 506 can be made of any material more radio-translucent than the calibration objects, for example. The calibration objects can be arranged in any pattern in the calibration object holder 506. For example, in some embodiments, the calibration objects can be arranged in a vertical line as illustrated in FIG. 5. In some embodiments, the calibration objects are arranged in the calibration object holder 506 to fall within the cone of x-rays generated by the x-ray source. In some embodiments, the vertical line can extend along a rotation axis 507, for example. In some embodiments, to simplify calibration object tracking through radiographs, the calibration objects are arranged to avoid coming close to one to another. This can be achieved by their vertical arrangement with some minimal spacing in the calibration object holder 506. In some embodiments, at least two calibration objects can be used. Any suitable number of calibration objects can be used, with some embodiments including 5 to 7, for example. In some embodiments, the calibration object holder 506 can be include any suitable shape such as a cylinder, for example, which can be drilled or otherwise punctured to produce one or more pits. In some embodiments, a calibration object can be arranged in a pit, for example. In some embodiments, the calibration objects can be affixed to an outer surface of the calibration object holder 506. In some embodiments, the calibration objects can be removable, or can be affixed with an adhesive such as glue, for example.

Figure 6A:
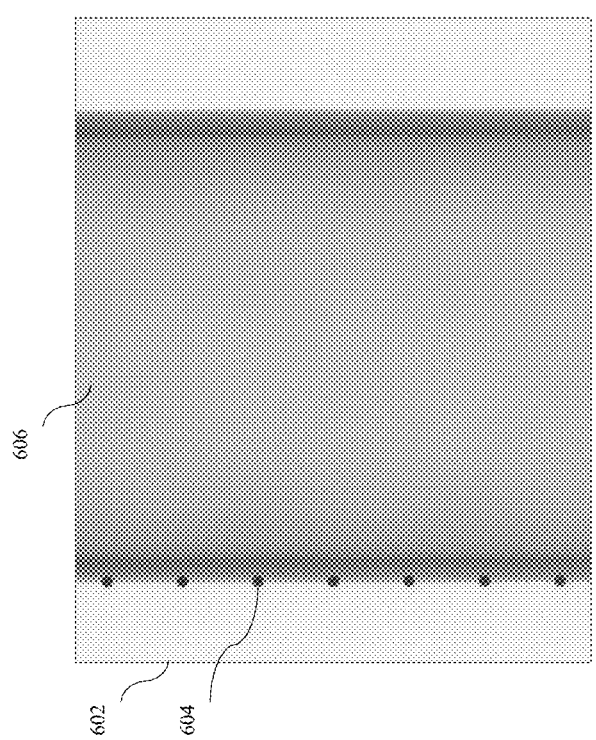
FIGS. 6(*a*), 6(*b*) and 6(*c*) are a 2D radiograph images that includes a calibration object projections and a calibration object holder projection.
Figure 6B:
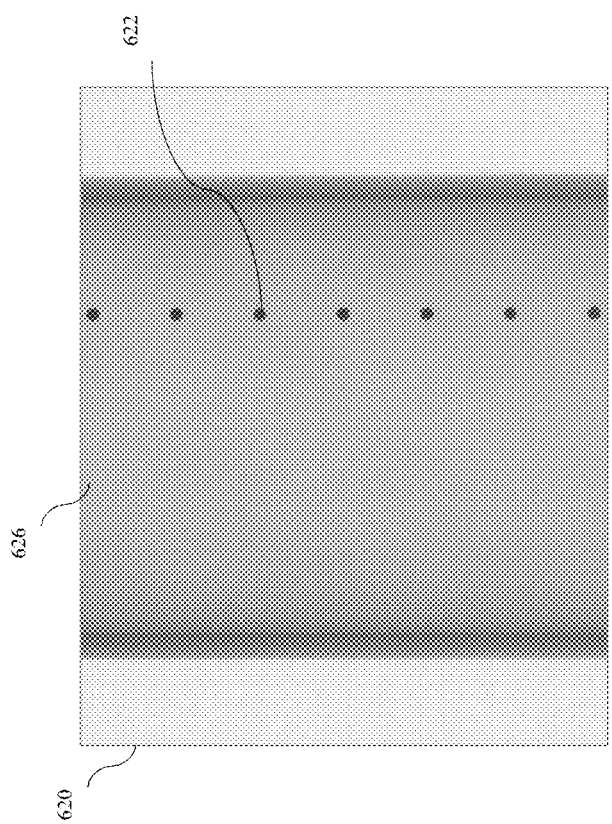
Figure 6C:
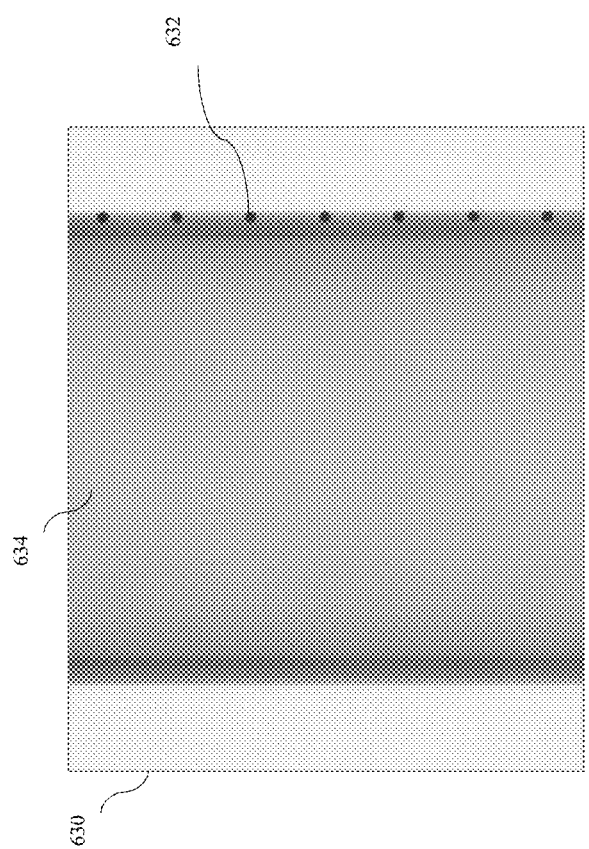

Some embodiments can include, for example, receiving a plurality of radiographs from the CT scanner, each of the plurality of radiographs including one or more calibration object projections. FIGS. 6(a) through 6(c) illustrate radiographs generated from the CT scanner after scanning the one or more calibration objects. FIG. 6(a) illustrates an example of a first radiograph 602 taken at a first rotational position during the CT scanning. The first radiograph 602 includes calibration object projections such as a first calibration object projection 604 of a calibration object 502 from FIG. 5 for example, along with the calibration object projections of the other calibration objects. Also appearing in the first radiograph 602 is the calibration object holder projection 606, for example, of the calibration object holder. FIG. 6(b) illustrates an example of a second radiograph 620 taken at a second rotational position during the CT scanning. The second radiograph 620 can include calibration object projections such as second calibration object projection 622 of calibration object 502 from FIG. 5, for example along with calibration object projections of the other calibration objects. Also appearing in the second radiograph 620 is the calibration object holder projection 626, for example, of the calibration object holder. FIG. 6(c) illustrates an example of a third radiograph 630 taken at a third rotational position during the CT scanning. The third radiograph 630 can include calibration object projections such as a third calibration object projection 632 of calibration object 502 from FIG. 5 along with calibration object projections of the other calibration objects. Also appearing in the third radiograph 630 is the calibration object holder projection 634, for example, of the calibration object holder. Three radiographs are shown only as an example. The computer-implemented method can receive at least four or more radiographs in some embodiments, for example. In some embodiments, the computer-implemented method can receive 600 or more radiographs of the calibration objects, for example. In some embodiments, the angles can span [0,360] degrees. In some embodiments, the computer-implemented method can rotate the object multiple times to generate additional radiographs.

In some embodiments, the computer-implemented can include determining one or more CT scanner calibration parameters from a plurality of calibration object projections in the plurality of radiographs. In some embodiments, this can include, for example, one or more of optionally preprocessing one or more of the radiographs, determining a location of each of the calibration object projections in a first projection, tracking a calibration object projection trajectory, determining a projective transformation of each calibration object projection, determining an axis of rotation projection, determining trajectory parameters from the projective transformation of each calibration object projection, determining the vertical shift, determining the detector distance, and determining the source distance.

In some embodiments, the computer-implemented method can optionally pre-process the radiographs. Pre-processing the radiographs can include, for example, converting a raw photo count $c(x,y)$ in each pixel $(x,y)$ of each projection into total attenuation coefficient $a(x,y)$.

In some embodiments, the computer-implemented method can receive a look-up table or other data structure containing empirically derived conversions from photon counts to attenuation coefficients. This can be done, for example, with polychromatic x-ray sources. The computer-implemented method can determine the attenuation coefficient for each corresponding radiograph pixel by matching the photon count to the attenuation coefficient in the look-up table. The computer-implemented method can then store or associate the attenuation coefficient with the corresponding radiograph pixel. Conventional CT scanners can provide the empirical conversion values which can be dependent on the particular CT scanner's x-ray source 142 and the type of material used. In some embodiments, the look-up table can be stored in a configuration file or a variable received by the computer-implemented method, for example.

Alternatively, in some embodiments, the computer-implemented method can determine an attenuation coefficient $a(x,y)$ theoretically for each corresponding radiograph pixel by converting the photon count $c(x,y)$ in each pixel $(x,y)$ of each radiograph as follows:

$$a(x,y)=\ln(I_0/c(x,y)) \text{ or } a(x,y)=\ln(I_0)-\ln(c(x,y))$$

where $I_0$ is a baseline photon count in the pixels of x-rays directly from the x-ray source 142, without passing through the physical object 146 which can in some embodiments, be the maximum possible photon count. This can be used with a monochromatic x-ray source, for example.

In some embodiments, the computer-implemented method can optionally determine attenuation coefficients empirically by receiving scanner coefficient values from the CT scanner and applying the values to a conversion function, for example. For example, the computer-implemented method can receive scanner coefficient values a,b,c,d,e, and f and apply the received scanner coefficient values to the conversion function $Y=a(b+cX+dX^2+eX^3+fX^4)$ to obtain each corresponding radiograph pixel's attenuation coefficient, where X is the attenuation coefficient of the pixel determined theoretically as described previously, Y is the attenuation coefficient to be obtained empirically, and a through f are the received scanner coefficient values. Other conversion functions can be used, and more or fewer coefficient values can be received. In one embodiment, the computer-implemented method can receive scanner coefficients such as a=1, b=0, c=0.75, d=0.25, e=0, f=0 for a Nikon CT scanner, for example. In another embodiment, the computer-implemented method can receive, scanner coefficients such as a=1, b=0, c=0.5, d=0.5, e=0, f=0 for a Nikon CT scanner, for example. The computer-implemented method can receive other scanner coefficient values and other CT scanner types and/or x-ray sources can be used. The scanner coefficients can be loaded by the computer-implemented method from a configuration file, for example in some embodiments. In some embodiments, the computer-implemented method can receive the scanner coefficients, calculate all attenuation coefficient values for photon counts (for example from 0 to the maximum possible photon count value) using the scanner coefficients, and store the photon count to attenuation coefficient conversions in a look up table or other data structure. In some embodiments, the computer-implemented method can store the look up table or other data structure in a configuration file, for example. In some embodiments, the computer-implemented method can load the configuration file as discussed previously.

Figure 7:
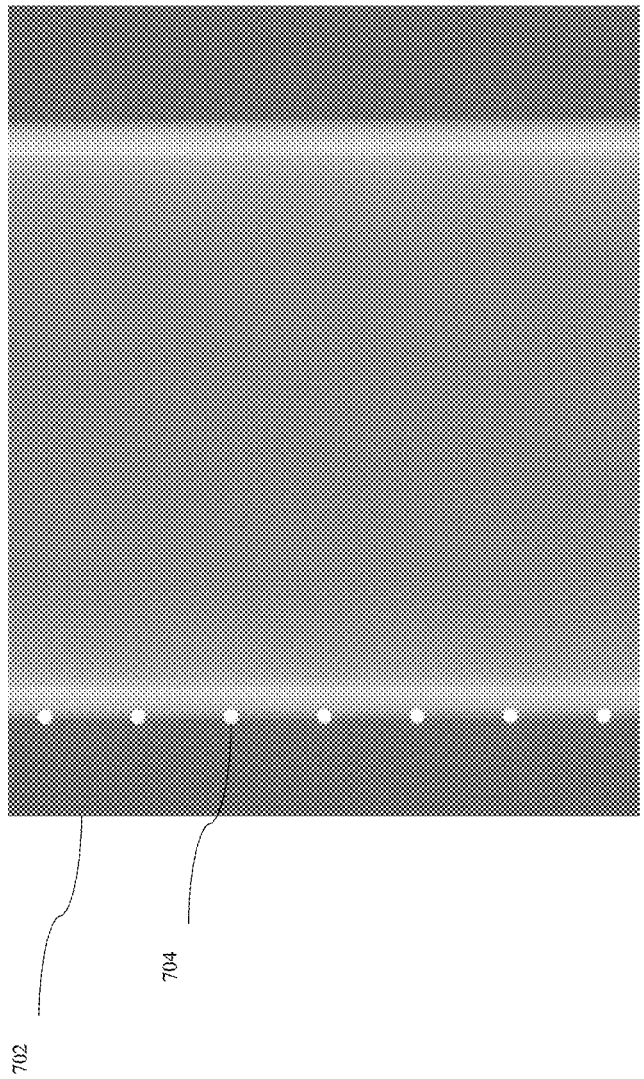
FIG. 7 shows a pre-processed 2D radio graph image that includes calibration objects and a calibration object holder.

FIG. 7 illustrates one example of single radiograph 702 whose raw photon count is converted to an attenuation coefficient. As illustrated in the figure, a calibration object projection 704 is converted to an attenuated photon count. In some embodiments, the computer-implemented method can pre-process one or more of the projected images.

In some embodiments, the computer-implemented method can determine a first projection position of each of the calibration object projections in a first projection. In some embodiments, the computer-implemented method can determine the location of each of the calibration object projections in the first projection by determining a histogram of pixel values in the first projection, determining the values of pixels covered by one of the calibration object projections from the histogram, finding any pixel in the projection with such value, locating the center of the first calibration object projection, determining the radius of the first calibration object projection, marking all pixels on a circle with found center and radius as processed, finding another pixel with a calibration object projection value among not-processed pixels, determining its center, marking its pixels as processed, and repeating the previous step until there are no more unprocessed pixels with calibration object projection values.

Figure 8:
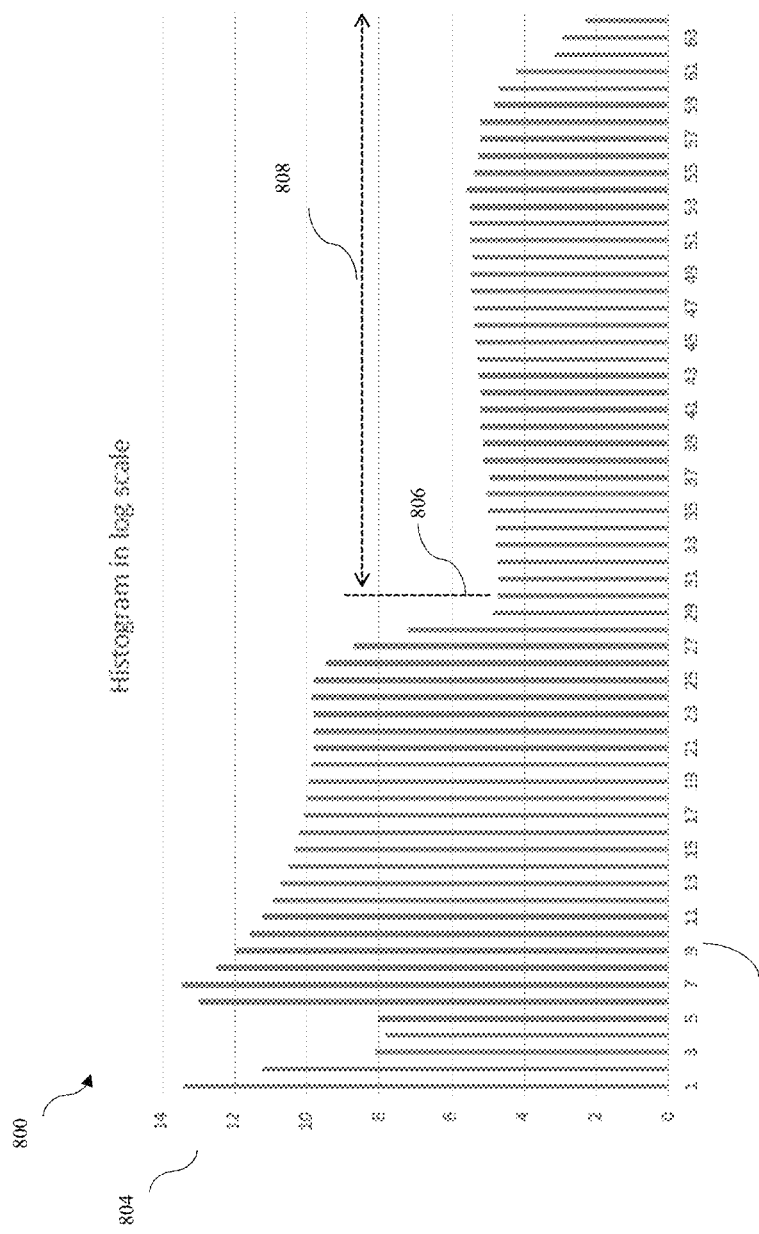
FIG. 8 shows a histogram in log scale of pixel intensity.

In some embodiments, the computer-implemented method can determine the first projection position of each of the calibration object projections in a first projection by determining a histogram of pixel values in the first projection. FIG. 8 illustrates a histogram 800 in log scale with an X-axis 802 of pixel intensity and a Y-axis 804 of the number of pixels at a particular intensity. Smaller X-axis 802 values can correspond to darker pixels and larger X-axis 802 values can correspond to brighter pixels. After pre-processing, the calibration object projection pixels are typically a brighter intensity than the calibration object holder projection pixels. Accordingly, the computer-implemented method can determine brighter pixels as being calibration object projection pixels. In some embodiments, the computer-implemented method can subdivide the range of all values on the pre-processed projection on a number of bins. In some embodiments, the number of bins can be 64, for example. Each bin along the X-axis 802 can correspond to an intensity level range. In some embodiments, the computer-implemented method can determine the minimum intensity 806 of the calibration object projection pixels as being in the center portion of the histogram. For example, the computer implemented method can determine the minimum intensity as being within the range of (first_bin+16, last_bin−16). The computer-implemented method can determine calibration object projection pixels 808 as those with pixel intensities greater than or equal to the minimum intensity 806 as illustrated in the figure, for example.

In some embodiments, the computer-implemented method can find the values of pixels belonging to one of the calibration object projections from the histogram. For example, the computer-implemented method can select a first pixel in the first projection that has a pixel intensity greater than or equal to the minimum intensity.

In some embodiments, the computer-implemented method can determine a first calibration object projection center based on the first pixel in the first projection. For example, the computer-implemented method can designate the first pixel as a rough first calibration object projection center. The computer-implemented method can determine a refined first calibration object projection center by selecting surrounding pixels within a radius of the rough first calibration object projection center and determining a center of mass of the surrounding pixels. The radius value can be set by a user in a configuration file in some embodiments, for example. The radius value can be, for example, 30 pixels. Other radius values can be used. In some embodiments, the computer-implemented method can determine the center of mass using techniques known in the art. For example, the computer-implemented method can determine a center of mass in some embodiments as follows:

$$c = \sum_i w_i r_i \Big/ \sum_i w_i$$

where $r_i$ is (x,y) coordinates of a pixel within search radius, and $w_i$ is the weight of the pixel. In some embodiments, the computer-implemented method can use the value of the pixel after preprocessing as the weight initially, for example. In some embodiments, the computer-implemented method can use the square of the pixel value, for example.

Each pixel weight can be taken as the value of the pixel after preprocessing (or as the square of the value). This can advantageously allow pixels of the ball to receive much higher weight than the pixels of the cylinder or air. This can also advantageously provide sub-pixel precision, for example. The computer-implemented method can replace the rough first calibration object projection center with the refined first calibration object projection center and perform the center of mass determination to determine the next refined first calibration object projection center. The process can be repeated several times, with each iteration determining a center of mass of surrounding pixels within the radius of the current first calibration object center to determine a more refined first calibration object center and replacing the current first calibration object center with a more refined first calibration object center. In some embodiments, the computer-implemented method can repeat the process 5 times, for example. Once the process is complete, the computer-implemented method has determined the first calibration object projection center in the first projection.

Figure 9:
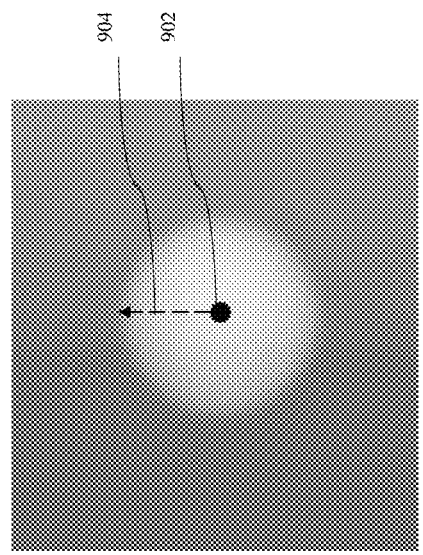
FIG. 9 shows a 2D radiograph of a calibration object projection.

In some embodiments, the computer-implemented method can determine a first calibration object projection radius in the first projection based on its center. As illustrated in FIG. 9, the computer-implemented method can start at the first calibration object projection center 902 and can evaluate adjacent pixel intensities along any direction 904 from the first calibration object projection center 902. If an adjacent pixel intensity is greater than or equal to the minimum intensity, then the computer-implemented method determines the adjacent pixel along the direction 904 to be part of the first calibration object projection. The computer-implemented method then evaluates the next adjacent pixel intensity. If, on the other hand, an adjacent pixel intensity is less than the minimum intensity, then the computer-implemented method determines the adjacent pixel along the direction 904 to be not be part of the first calibration object projection and stops evaluating any more adjacent pixels along the direction 904. The computer-implemented method can set the first calibration object projection radius as the number of adjacent pixels along the direction 904 from the first calibration object projection center. The computer-implemented method can designate all pixels enclosed by a circle having the first calibration object projection center 902 and with a first calibration object projection radius as processed in some embodiments.

In some embodiments, the computer-implemented method can determine other calibration object projections in the first projection in a similar manner. For example, in some embodiments, the computer-implemented method can determine a second pixel in the first projection that has a pixel intensity greater than or equal to the minimum intensity and that is among not-processed pixels, determine its center, radius, and circle and mark its pixels as processed as described previously. The computer-implemented method can thus determine the position of each calibration object projection in the first projection in some embodiments for example.

In some embodiments, the computer-implemented method can track each calibration object projection from the plurality of radiographs to determine a calibration object projection trajectory. In some embodiments, the computer-implemented method can determine the position of each calibration object projection in radiographs other than the first radiograph based on its position in one or two of its previous radiographs. In the case where a position of the first calibration object projection is known in only one previous radiograph, the computer-implemented method can determine a current radiograph position as the same as the previous radiograph position. For example, in the case of determining a calibration object projection's position in the second projection, the computer-implemented method can determine the approximate second radiograph position to be the same as the first radiograph position of the calibration object projection. If the position of the calibration object projection is known in the two prior radiographs p-1 (position of the calibration object projection in the previous radiograph) and p-2, (position of the calibration object in the radiograph before the previous radiograph), then the computer-implemented method can determine 2p-1−p-2 as a starting approximation of the calibration object projection position in the current projection. In some embodiments, the computer-implemented method can then determine the calibration object projection's position using the approximation of the calibration object projection position and determining the current calibration object projection center and radius by performing the steps described with respect to determining the center and radius of the first calibration object projection. Applying these tracking techniques can, for example, advantageously account for motion of each calibration object projection between projections.

Figure 10A:
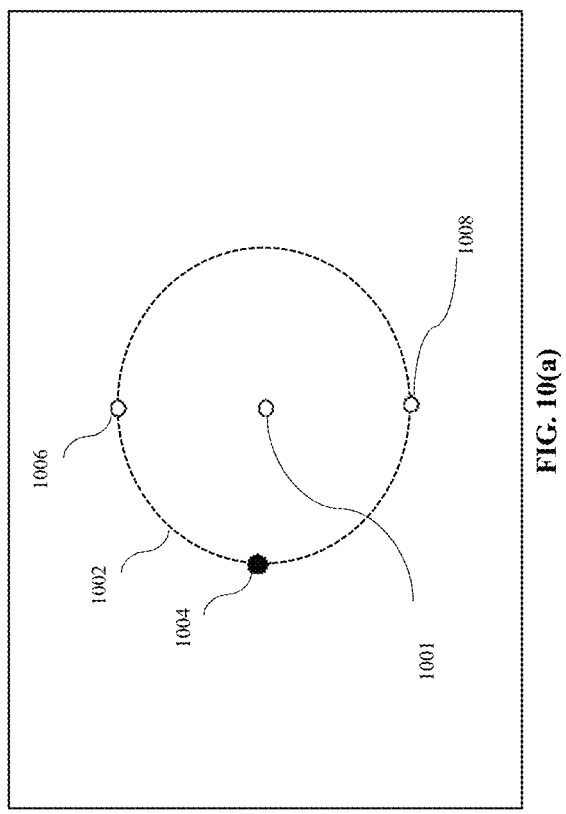
FIG. 10(*a*) shows a view of a plane of rotation looking down the axis of rotation.

In some embodiments, the computer-implemented method can determine a projective transformation of each calibration object projection across all radiographs. A projective transformation can be used to describe or map a relationship between points on two different planes, for example. FIG. 10(a) illustrates a view looking down an axis of rotation 1001 a plane of rotation 1002 of a calibration object 1004 as it is rotated on the rotation table. Calibration object positions 1006 and 1008 are also on the plane of rotation 1002. The plane of rotation 1002 establishes the calibration object's location during scanning and is orthogonal to the axis of rotation 1001.

Figure 10B:
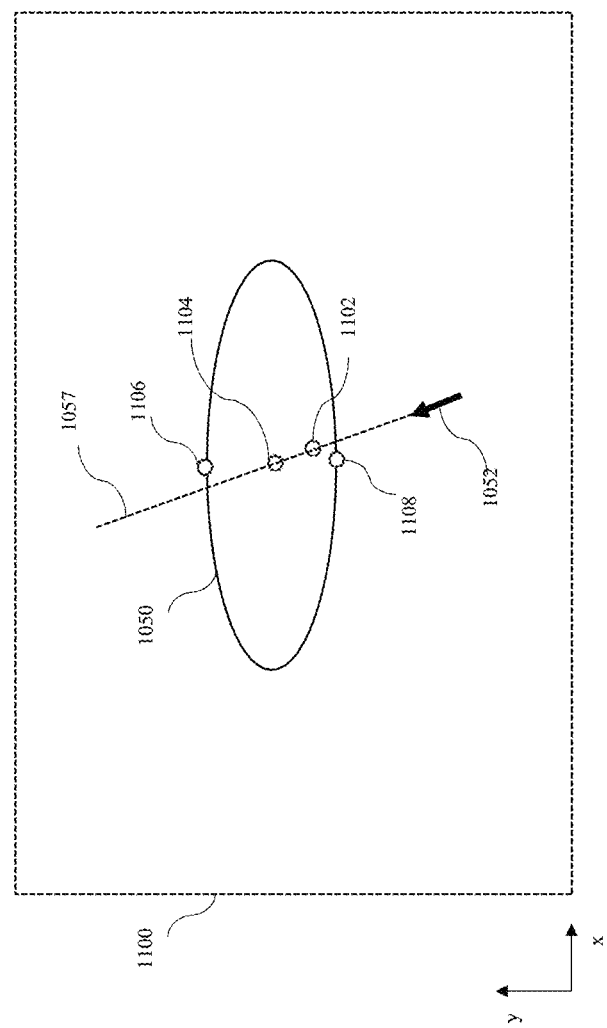

FIG. 10(b) illustrates an example of a detector plane 1100. The computer-implemented method can determine a projective transformation that maps one or more points from the plane of rotation 1002 from FIG. 10(a) to a point on the detector plane 1100 of FIG. 10(b). As an example, calibration object positions 1006 and 1008 from FIG. 10(a) can map to first and second calibration object projections 1106 and 1108, respectively on the detector plane 1100 illustrated in FIG. 10(b). The projective transformation can map a relationship between a physical location q of a calibration object in the plane of rotation and the corresponding calibration object projection position, p, on the detector plane, for example. In some embodiments, the relationship can be expressed as the projective transformation (or homography):

$$p = H(q) = \frac{Aq+b}{1+c^T q}$$

where A is a 2×2 matrix and b, c are 2×1 vectors. In some embodiments, the matrix A can reflect changes in rotation and scale of the q plane. Vector b can represent a translational offset, which can be a projected center of circle trajectory 1102, for example, as shown in FIG. 10(b). In some embodiments, the computer-implemented method can choose a coordinate system in the plane of rotation of the calibration object to have $q^T=(\cos \phi, \sin \phi)$, where $\phi$ is the degree of table rotation, or rotational degree 214 as illustrated in FIG. 4(a). The degree of table rotation is known for each radiograph and is relative to the first radiograph. In some embodiments, the computer-implemented method can determine the calibration object projection position p from the tracking step described previously.

In some embodiments, the computer-implemented method can determine the best projective transformation for each calibration object. For example, given a number of pairs $(p_i, q_i)$ the computer-implemented method can determine the best A, b, c by solving linear overdetermined system:

$$(1+c^T q_i)p_i = Aq_i + b$$

On the first iteration the weight of each equation in the system can be 1. On the successive iterations, the computer-implemented method can determine the weight as:

$$\frac{1}{1+c^T q_i}$$

with the value of c from the previous iteration. In some embodiments, the computer-implemented method can utilize another method of estimating A, b, and c as described in *Efficiently Estimating Projective Transformations*, Richard Radke, Peter Ramadge Department of Electrical Engineering, Princeton University, and Tomio Echigo, IBM Research, Tokyo Research Laboratory, Jun. 27, 2001, which is hereby incorporated by reference in its entirety.

In some embodiments, the computer-implemented method can determine one or more calibration parameters from the projective transformation of each calibration object across all radiographs. For example, in some embodiments, the computer-implemented method can determine projected rotation axis parameters. In some embodiments, the computer-implemented method can determine the projected rotation axis parameters before determining any other calibration parameters. For example, a projective transformation of a rotation plane center of circle trajectory $q^T=(0, 0)$ 1001 in FIG. 10(a) of each calibration object projection can be mapped as a projected center of circle trajectory b 1102 in FIG. 10(b) on the detector, and $u_0$ and $\alpha$ can be determined as linear regression coefficients of the form:

$$b_{x,i} = u_0 + t b_{y,i}, t = \tan(\alpha)$$

Figure 11:
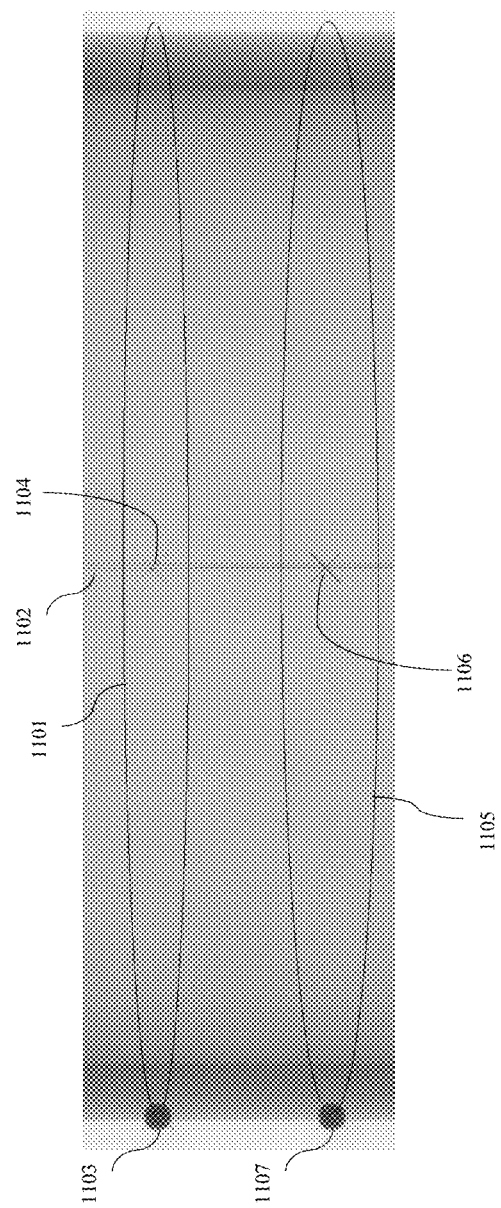
FIG. 11 shows an illustration of a 2D radiograph image showing calibration object projections.

The overdetermined system (if the number of calibration object projections is more than 2) can be solved by the computer-implemented method using the least-squares method known in the art to determine $u_0$ and the inclination angle $\alpha$. As illustrated in FIG. 11, a first calibration object projection trajectory 1101 is established by a first calibration object projection 1103 and a second calibration object projection trajectory 1105 is established by a second calibration object projection 1107. The rotation axis projection 1102 passes through projections of trajectory centers such as first projected center of circle trajectory 1104 and second projected center of circle trajectory 1106. The computer-implemented method can determine the projected rotation axis from all of the center of circle trajectories of the calibration object projections.

In some embodiments, the computer-implemented method can determine trajectory parameters from the projective transformation. For example, the computer-implemented method can construct inverse projective transformations $H^{-1}$ (mapping from a detector plane to the plane of rotation of the calibration object) of each calibration object in some embodiments. For example, the computer-implemented method can determine the inverse projective transformation for each calibration object projection. The inverse projective transformation can be found as:

$$H^{-1}(p) = \frac{(1-c^T A^{-1}b)(A-bc^T)^{-1}p - A^{-1}b}{1-(1-c^T A^{-1}b)c^T(A-bc^T)^{-1}p}$$

In some embodiments, the computer-implemented method can determine s as follows:

Let n be a unit direction vector of the projected axis of rotation

Figure 12:
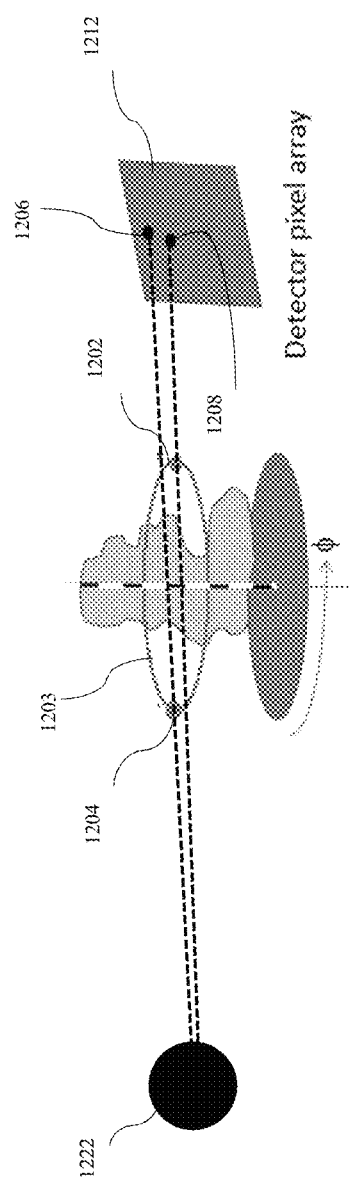
FIG. 12 shows a schematic of a close and far points from a detector on a rotational plane.

For each calibration object projection, let $s'=H^{-1}(b+n)$, $s=s'/|s'|$, where $H^{-1}$ is the inverse projective transformation, b is the projected center of circle trajectory, and s is a point on the circle trajectory of the calibration object which is sought as illustrated in FIG. 12.

The computer-implemented method can determine a geometric center of each trajectory projection e as follows:

$$e = \frac{1}{2}(H(s) + H(-s))$$

where e is a geometric center of the calibration object projection trajectory.

If the dot product (e−b, n)<0, then let s:=−s. −s is the point on the circle opposite to s. One of them is the closest and the other—the farthest from the detector. Which one is which depends on the sign of the dot product (e−b, n). For example, if (e−b,n)>0 then computed s is the most distant point on the circle from the detector. If (e−b,n)<0 then computed s is the closest point to the detector, and the computer-implemented method changes s=−s to again have in s the most distant point on the circle from the detector.

FIG. 10(b) illustrates a calibration object projection trajectory 1050, unit direction vector n 1052, projected axis of rotation 1057 projected center of circle trajectory b 1102 with geometric center of trajectory projection e 1104. As can be seen in the figure, the projected center of circle trajectory b is not the same as the geometric center of the trajectory projection e 1104.

The computer-implemented method can determine for each calibration object two of its calibration object projections: its closest position, H(s), and farthest position, H(−s) from the detector. In some embodiments, the computer-implemented method can determine the closest position and farthest position after determining the projected center of circle trajectory b-point and the rotation axis with the directional vector n and projective transformation H as follows:

FIG. 12 illustrates determining the closest point −s 1202 on the plane of rotation 1203 to the detector 1212 and furthest point S 1204 to the detector 1212. Closest point −s 1202 can be determined from calibration object projection 1208 (H(−s)) and furthest points 1204 can be determined from calibration object projection 1206 (H(s)). Also shown in x-ray source 1222.

The computer-implemented method can determine for each calibration object two of its calibration object projections corresponding to two positions of the calibration object equidistant from the detector H(l) and H(−l). H(s) is a calibration object projection corresponding to most distant position of the calibration object from the detector. H(−s) is a calibration object projection corresponding to closest position of the calibration object to the detector, $$\phi = \pi + \tan^{-1}\frac{s_y}{s_x}$$

is the angle of the rotation table where the calibration object reaches its closest position to the detector. The computer-implemented method can set $l^T=(s_y, -s_x)$ so that H(l) and H(−l) are two projections of the calibration object corresponding to two positions of the calibration object equidistant from the detector.

In some embodiments, the computer-implemented method can construct a system of linear equations to determine vertical shift and source-to-detector distance: D and $v_0$ For example, in some embodiments, the computer-implemented method can determine the vertical shift $v_0$ and source distance D as follows: For the calibration #i, it can be satisfied $$(e_i, n) = n_y v_0 - n_x u_0 + D\frac{|H_i(s_i) - H_i(-s_i)|}{|H_i(l_i) - H_i(-l_i)|}$$

The computer-implemented method can determine parameters D and $v_0$ using least-squares method from the equations for all calibration objects in some embodiments, for example. At least 2 calibration objects are required to find them. For example, given a distance m between a pair of calibration objects (e.g. calibration object #0 and calibration object #1) in real world, find the source-to-axis distance d by the formula:

$$d = \frac{Dm}{\sqrt{k_0 + k_1 + k_2 - k_3}}$$

Where $$k_0 = (b_1 - b_0)^2,$$

$$k_1 = \frac{1}{4}(H_0(l_0) - H_0(-l_0))^2,$$

$$k_2 = \frac{1}{4}(H_1(l_1) - H_1(-l_1))^2,$$

$$k_3 = 2k_1 k_2 \cos(\phi_0 - \phi_1)$$

The variables b, c, e, n, l, s, p, q as used in formulas in this disclosure are vectors, for example.

Once the calibration parameters are determined, the computer-implemented method can output the parameters to an algorithm that performs CT reconstruction of the projected images. In some embodiments, the calibration parameters can be output along with the projected images to the CT reconstruction algorithm.

In some embodiments, the calibration parameters can be determined as necessary. For example, in some cases, the CT scanner may require calibration only after change in the position of the rotating stage. In some cases, the CT scanner may require calibration once a week, or other period.

In some embodiments, it may be desirable to use a minimum number of radiographs as few as possible to accelerate calibration, for example, 40 radiographs. In some embodiments, the computer-implemented method can determine the one or more CT scanner calibration parameters by considering all of the radiographs. In some embodiments, the computer-implemented method can advantageously determine the one or more CT scanner calibration parameters even if every calibration object does not appear as a calibration object projection in every radiograph. In some embodiments, the computer-implemented method can advantageously determine the location of each calibration object even if mounted on a cylinder with thick walls.

In some embodiments, the computer-implemented method can perform one or more of the steps and/or features disclosed herein on unreconstructed radiographs, prior to CT reconstruction of one or more radiographs, for example.

In some embodiments, the computer-implemented method can determine a rotation direction of the calibration object in the rotation plane from the plurality of radiographs. The CT scanning system. For example, in some embodiments, 1. The computer-implemented method determines S, the point on the rotation circle most distant from the detector for each calibration object as described previously.

2. The computer-implemented method can determine two sequential projection images of the calibration object projection at the rotation angle close to S.

3. The computer-implemented method can determine a calibration object projection movement from the radiograph K to radiograph K+1. For example, the computer-implemented method can determine (calibration object projection center in radiograph K+1) minus (computer-object projection center in radiograph number K). The calibration object projection movement close to S is the largest of all other movements of the same calibration object projection in other consecutive radiographs.

4. The computer-implemented method can determine a sum of the calibration object projection movements of all calibration object projections from step 3.5. If the summed movement has horizontal component from left to right, then the scanner rotates the object in counter-clockwise direction. If the summed movement has horizontal component from right to left, then the scanner rotates the object in clockwise direction.

In some embodiments, the computer-implemented method can provide the rotation direction to the reconstruction algorithm. The reconstruction algorithm can use the rotation direction during its tomographic reconstruction of the radiographs. One or more advantages of determining the rotation direction from the radiographs is the process can be automated and reduces errors.

One or more advantages of one or more features can include, for example, improved precision and accuracy. One or more features disclosed herein can, for example process more than 4 radiographs, which can improve the precision and accuracy of the CT calibration calculations, for example. One or more features disclosed herein, can, for example, process radiographs with calibration object projections in multiple locations/positions, which can provide flexibility with respect to calibration object locations and arrangements. One advantage of one or more features disclosed herein can include, for example, determining CT calibration parameters even if a calibration object projection does not appear in all radiographs. One advantage of one or more features disclosed herein can include, for example, determining CT calibration parameters even if a calibration object projection appears in only a few radiographs, and even if no radiographs include extreme calibration object projection positions relative to the detector. One advantage of one or more features disclosed herein can include, for example, determining CT calibration parameters even with inexact position of calibration objects in some radiographs. One advantage of one or more features disclosed herein can include, for example, determining CT calibration parameters of a cone-beam CT scanner, which can require more complex 3D computations than fan-beam CT scanners, which can require 2D computations. One advantage of one or more features disclosed herein can include, for example, determining CT calibration parameters without relying on iterative and/or brute force search of a list of candidates, thereby improving speed. Iterative searches may not guarantee the amount of time necessary to find the solution, or that one will be found at all. One advantage of one or more features disclosed herein can include, for example, determining CT calibration parameters after a finite number of operations.

Figure 13:
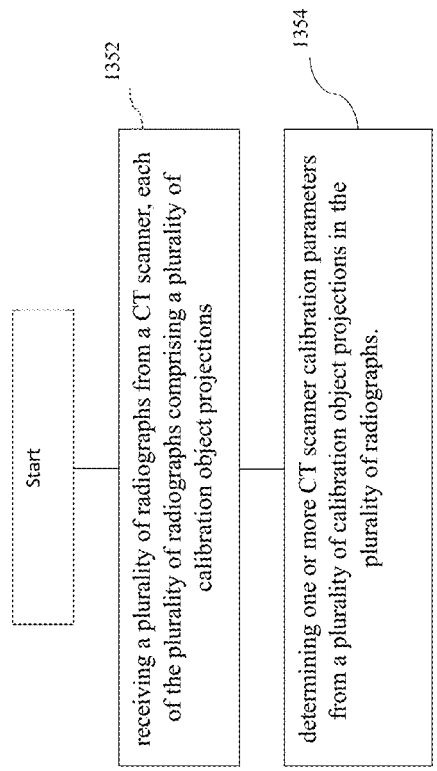
FIG. 13 shows a flowchart of a method in some embodiments.

Some embodiments include a method of determining CT calibration settings. As illustrated in FIG. 13 the method can include receiving a plurality of radiographs from a CT scanner, each of the plurality of radiographs comprising a plurality of calibration object projections at 1352; and determining one or more CT scanner calibration parameters from a plurality of calibration object projections in the plurality of radiographs at 1354.

The computer-implemented method can include one or more features described in the present disclosure.

The computer-implemented method can include several optional features. For example, the calibration objects can include a plurality of spherical objects arranged in a calibration object holder. The CT scanner can be a cone beam scanner. The one or more CT scanner calibration parameters from the projective transformation comprise one or more from the group consisting of a projected horizontal axis shift, a projected rotational axis inclination angle, a vertical shift, detector distance, and axis of rotation distance. Determining one or more CT scanner calibration parameters can include determining a first projection position of each of the plurality of calibration objects in a first projection of the plurality of radiographs. Determining the first projection position can include determining a histogram of pixel values in the first projection. The computer-implemented method can additionally further include tracking the plurality of calibration objects in the plurality of radiographs. The one or more CT scanner calibration parameters can include one or more trajectory parameters of each calibration object from the projective transformation. The computer-implemented method can further include pre-processing the plurality of radiographs. The computer-implemented method can further include determining a rotation direction from the plurality of radiographs.

Some embodiments can include a non-transitory computer readable medium storing executable computer program instructions to determine CT calibration settings, the computer program instructions including instructions for: receiving a plurality of radiographs from a CT scanner, each of the plurality of radiographs comprising a plurality of calibration object projections; and determining one or more CT scanner calibration parameters from a plurality of calibration object projections in the plurality of radiographs.

The non-transitory computer readable medium storing executable computer program instructions to determine CT calibration settings can include one or more features described in the present disclosure.

Some embodiments can include a system for determining CT calibration settings, including: a processor; a computer-readable storage medium comprising instructions executable by the processor to perform steps comprising: receiving a plurality of radiographs from a CT scanner, each of the plurality of radiographs comprising a plurality of calibration object projections; and determining one or more CT scanner calibration parameters from a plurality of calibration object projections in the plurality of radiographs.

The system can implement one or more features/methods described in the present disclosure.

The system can implement optional features. The system can include several optional features. For example, the calibration objects can include a plurality of spherical objects arranged in a calibration object holder. The CT scanner can be a cone beam scanner. The one or more CT scanner calibration parameters from the projective transformation comprise one or more from the group consisting of a projected horizontal axis shift, a projected rotational axis inclination angle, a vertical shift, detector distance, and axis of rotation distance. Determining one or more CT scanner calibration parameters can include determining a first projection position of each of the plurality of calibration objects in a first projection of the plurality of radiographs. Determining the first projection position can include determining a histogram of pixel values in the first projection. The system can additionally further include tracking the plurality of calibration objects in the plurality of radiographs. The one or more CT scanner calibration parameters can include one or more trajectory parameters of each calibration object from the projective transformation. The system can further include pre-processing the plurality of radiographs. The system can further include determining a rotation direction from the plurality of radiographs.

Figure 14:
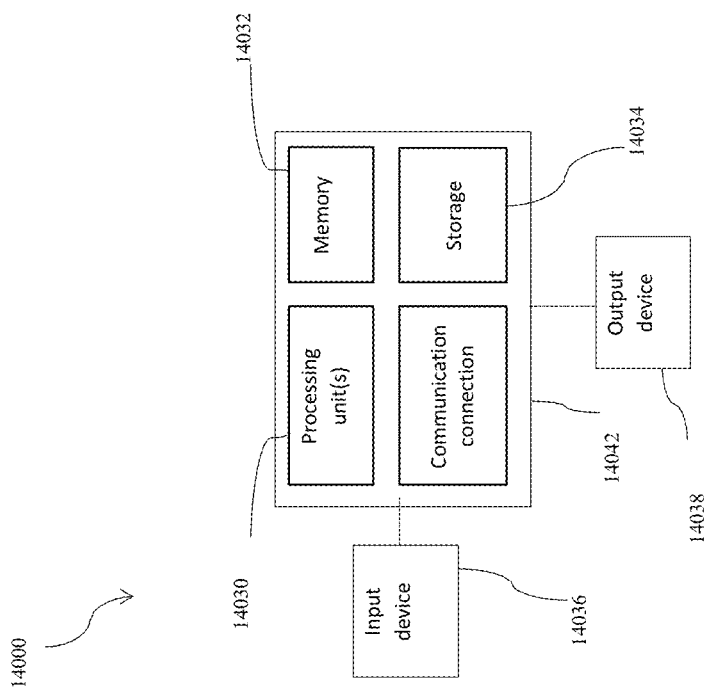
FIG. 14 shows a schematic diagram of a system in some embodiments.

FIG. 14 illustrates a processing system 14000 in some embodiments. The system 14000 can include a processor 14030, computer-readable storage medium 14034 having instructions executable by the processor to perform one or more steps described in the present disclosure. In some embodiments, the radiographs can optionally be provided by a CT scanner, for example. In some embodiments, the system 14000 can provide one or more CT calibration parameters and optionally one or more radiographs.

One or more of the features disclosed herein can be performed and/or attained automatically, without manual or user intervention. One or more of the features disclosed herein can be performed by a computer-implemented method. The features—including but not limited to any methods and systems—disclosed may be implemented in computing systems. For example, the computing environment 14042 used to perform these functions can be any of a variety of computing devices (e.g., desktop computer, laptop computer, server computer, tablet computer, gaming system, mobile device, programmable automation controller, video card, etc.) that can be incorporated into a computing system comprising one or more computing devices. In some embodiments, the computing system may be a cloud-based computing system.

For example, a computing environment 14042 may include one or more processing units 14030 and memory 14032. The processing units execute computer-executable instructions. A processing unit 14030 can be a central processing unit (CPU), a processor in an application-specific integrated circuit (ASIC), or any other type of processor. In some embodiments, the one or more processing units 14030 can execute multiple computer-executable instructions in parallel, for example. In a multi-processing system, multiple processing units execute computer-executable instructions to increase processing power. For example, a representative computing environment may include a central processing unit as well as a graphics processing unit or co-processing unit. The tangible memory 14032 may be volatile memory (e.g., registers, cache, RAM), non-volatile memory (e.g., ROM, EEPROM, flash memory, etc.), or some combination of the two, accessible by the processing unit(s). The memory stores software implementing one or more innovations described herein, in the form of computer-executable instructions suitable for execution by the processing unit(s).

A computing system may have additional features. For example, in some embodiments, the computing environment includes storage 14034, one or more input devices 14036, one or more output devices 14038, and one or more communication connections 14037. An interconnection mechanism such as a bus, controller, or network, interconnects the components of the computing environment. Typically, operating system software provides an operating environment for other software executing in the computing environment, and coordinates activities of the components of the computing environment.

The tangible storage 14034 may be removable or non-removable, and includes magnetic or optical media such as magnetic disks, magnetic tapes or cassettes, CD-ROMs, DVDs, or any other medium that can be used to store information in a non-transitory way and can be accessed within the computing environment. The storage 14034 stores instructions for the software implementing one or more innovations described herein.

The input device(s) may be, for example: a touch input device, such as a keyboard, mouse, pen, or trackball; a voice input device; a scanning device; any of various sensors; another device that provides input to the computing environment; or combinations thereof. For video encoding, the input device(s) may be a camera, video card, TV tuner card, or similar device that accepts video input in analog or digital form, or a CD-ROM or CD-RW that reads video samples into the computing environment. The output device(s) may be a display, printer, speaker, CD-writer, or another device that provides output from the computing environment.

The communication connection(s) enable communication over a communication medium to another computing entity. The communication medium conveys information, such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

Any of the disclosed methods can be implemented as computer-executable instructions stored on one or more computer-readable storage media 14034 (e.g., one or more optical media discs, volatile memory components (such as DRAM or SRAM), or nonvolatile memory components (such as flash memory or hard drives)) and executed on a computer (e.g., any commercially available computer, including smart phones, other mobile devices that include computing hardware, or programmable automation controllers) (e.g., the computer-executable instructions cause one or more processors of a computer system to perform the method). The term computer-readable storage media does not include communication connections, such as signals and carrier waves. Any of the computer-executable instructions for implementing the disclosed techniques as well as any data created and used during implementation of the disclosed embodiments can be stored on one or more computer-readable storage media 14034. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, Python, JavaScript, Adobe Flash, or any other suitable programming language. Likewise, the disclosed technology is not limited to any particular computer or type of hardware. Certain details of suitable computers and hardware are well known and need not be set forth in detail in this disclosure.

It should also be well understood that any functionality described herein can be performed, at least in part, by one or more hardware logic components, instead of software. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

In view of the many possible embodiments to which the principles of the disclosure may be applied, it should be recognized that the illustrated embodiments are only examples and should not be taken as limiting the scope of the disclosure.

What is claimed is:

1. A method of determining CT calibration settings, the method comprising:
   receiving a plurality of radiographs from a CT scanner, each of the plurality of radiographs comprising a plurality of calibration object projections; and
   determining one or more CT scanner calibration parameters from a plurality of calibration object projections in the plurality of radiographs prior to CT reconstruction.

2. The method of claim 1, wherein the calibration object projections are projections of spherical calibration objects arranged in a calibration object holder.

3. The method of claim 1, wherein the CT scanner is a cone beam scanner.

4. The method of claim 1, wherein the one or more CT scanner calibration parameters comprise one or more from the group consisting of a projected horizontal axis shift, a projected rotational axis inclination angle, a vertical shift, detector distance, and axis of rotation distance.

5. The method of claim 1, wherein determining one or more CT scanner calibration parameters comprises determining a first projection position of each of the plurality of calibration objects in a first projection of the plurality of radiographs.

6. The method of claim 5, wherein determining the first projection position comprises determining a histogram of pixel values in the first projection.

7. The method of claim 1, further comprising tracking the plurality of calibration objects in the plurality of radiographs.

8. The method of claim 1, further comprising determining a rotation direction from the plurality of radiographs.

9. The method of claim 1, further comprising pre-processing the plurality of radiographs.

10. A system for determining CT calibration settings, comprising:
    a processor; and
    a non-transitory computer-readable storage medium comprising instructions executable by the processor to perform steps comprising:
      receiving a plurality of radiographs from a CT scanner, each of the plurality of radiographs comprising a plurality of calibration object projections; and
      determining one or more CT scanner calibration parameters from a plurality of calibration object projections in the plurality of radiographs prior to CT reconstruction.

11. The system of claim 10, wherein the calibration object projections are projections of spherical calibration objects arranged in a calibration object holder.

12. The system of claim 11, further comprising tracking the plurality of calibration objects in the plurality of radiographs.

13. The system of claim 10, wherein the CT scanner is a cone beam scanner.

14. The system of claim 10, wherein the one or more CT scanner calibration parameters from the projective transformation comprise one or more from the group consisting of a projected horizontal axis shift, a projected rotational axis inclination angle, a vertical shift, detector distance, and axis of rotation distance.

15. The system of claim 10, wherein determining one or more CT scanner calibration parameters comprises determining a first projection position of each of the plurality of calibration objects in a first projection of the plurality of radiographs.

16. The system of claim 15, wherein determining the first projection position comprises determining a histogram of pixel values in the first projection.

17. The system of claim 10, further comprising tracking the plurality of calibration objects in the plurality of radiographs.

18. The system of claim 10, further comprising determining a rotation direction from the plurality of radiographs.

19. The system of claim 10, further comprising pre-processing the plurality of radiographs.

20. A non-transitory computer readable medium storing executable computer program instructions to determine CT calibration settings, the computer program instructions comprising instructions for:
    receiving a plurality of radiographs from a CT scanner, each of the plurality of radiographs comprising a plurality of calibration object projections; and
    determining one or more CT scanner calibration parameters from a plurality of calibration object projections in the plurality of radiographs prior to CT reconstruction.

* * * * *